United States Patent [19]

Knöfel et al.

[11] Patent Number: 4,587,058

[45] Date of Patent: May 6, 1986

[54] DIISOCYANATES OF THE DIPHENYL METHANE SERIES AND PROCESSES FOR THE PRODUCTION THEREOF

[75] Inventors: Hartmut Knöfel, Odenthal-Erberich; Michael Brockelt, Bergisch Gladbach, both of Fed. Rep. of Germany

[73] Assignee: Bayer Aktiengesellschaft, Leverkusen, Fed. Rep. of Germany

[21] Appl. No.: 290,983

[22] Filed: Aug. 7, 1981

[30] Foreign Application Priority Data

Aug. 26, 1980 [DE] Fed. Rep. of Germany ....... 3032128

[51] Int. Cl.[4] ................. C07C 118/02; C07C 119/048
[52] U.S. Cl. ...................................... 560/347; 560/359
[58] Field of Search ................. 260/453 PH, 453 AM

[56] References Cited

U.S. PATENT DOCUMENTS

| | | | |
|---|---|---|---|
| 2,683,144 | 7/1954 | Balon et al. | 260/453 AR |
| 3,152,162 | 10/1964 | Fischer et al. | 260/453 |
| 3,180,883 | 4/1965 | Case | 260/453 AM |
| 3,255,226 | 6/1966 | McShane, Jr. | 260/453 AM |
| 3,375,264 | 3/1968 | Sayigh et al. | 260/453 AM |
| 3,644,457 | 2/1972 | König et al. | 260/453 SP |

FOREIGN PATENT DOCUMENTS

| | | |
|---|---|---|
| 1901993 | 8/1970 | Fed. Rep. of Germany . |
| 1013710 | 12/1965 | United Kingdom . |
| 1117066 | 6/1968 | United Kingdom . |
| 1163264 | 9/1969 | United Kingdom . |

Primary Examiner—Dolph H. Torrence
Attorney, Agent, or Firm—Gene Harsh; Joseph C. Gil; Lyndanne M. Whalen

[57] ABSTRACT

A diisocyanate corresponding to the general formula:

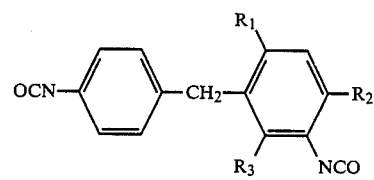

in which $R_1$, $R_2$ and $R_3$ represent hydrogen or a $C_2$–$C_{12}$ alkyl group provided that two of the radicals $R_1$, $R_2$ and $R_3$ represent hydrogen and the third represents an alkyl group containing from 2 to 12 carbon atoms. Mixtures of diisocyanates in which the described diisocyanate is a major substituent are also within the scope of this disclosure. Such compounds and mixtures are made by reacting a nitrobenzyl halide, an unsubstituted benzyl halide or a benzyl alcohol in the presence of a Friedel-Crafts catalyst with an alkylbenzene or a nitroalkylbenzene and then converting the nitro groups to amino groups by hydrogenation or reduction. The thus-produced amino compound is then phosgenated to form the diisocyanate.

The compounds and mixtures of the present invention are useful in the production of polyurethane plastics.

12 Claims, No Drawings

DIISOCYANATES OF THE DIPHENYL METHANE SERIES AND PROCESSES FOR THE PRODUCTION THEREOF

BACKGROUND OF THE INVENTION

The present invention relates to alkyl-substituted diisocyanates of the diphenyl methane series having isocyanate groups in the 3,4' position and to processes for the production of such alkyl-substituted diisocyanates.

The organic polyisocyanates which are technically and economically important as starting materials in the production of polyurethane plastics include 2,4-diisocyanato-toluene and mixtures thereof with 2,6-diisocyanato-toluene (TDI), 4,4'-diisocyanato-diphenyl methane and mixtures thereof with 2,2'- or 2,4'-diisocyanato-diphenyl methane and/or with homologues of higher functionality (MDI). Although these aromatic polyisocyanates are universally used in large quantities for the production of polyurethane plastics (particularly foams and elastomers) they are attended by certain disadvantages. TDI, for example, has a high vapor pressure and for physiological reasons requires strict safety measures in processing. MDI, particularly 4,4'-diisocyanato-diphenyl methane which is generally present as the main component in polyisocyanate mixtures of the diphenyl methane series tends to crystallize and is a solid at room temperature. Therefore, MDI raw materials often have to be liquefied before processing. This liquification is accomplished either by heating the MDI material to a temperature above the melting point of 4,4'-diisocyanato-diphenyl methane or by chemical modification such as partial urethanization (See for example U.S. Pat. No. 3,644,457) or partial carbodiimidization (See for example U.S. Pat. No. 3,152,162).

It would therefore be advantageous to have aromatic polyisocyanates which could be used in making polyurethanes having properties comparable to those made from TDI and MDI but which need not be liquified before use and are not as physiologically hazardous as these prior art materials.

SUMMARY OF THE INVENTION

It is an object of the present invention to provide an aromatic polyisocyanate which may be used in making polyurethanes having properties comparable to those made from prior art materials which polyisocyanates are not as physiologically hazardous as known materials.

It is another object of the present invention to provide an aromatic polyisocyanate which may be used in making polyurethanes without first being liquified.

It is a further object of the present invention to provide an aromatic polyisocyanate having isocyanate groups which differ in reactivity from the isocyanate groups present in prior art materials such as 4,4'-diisocyanato-diphenyl methane.

It is yet another object of the present invention to provide diisocyanate which may be used to produce a polyurethane having rigid segments corresponding to the hydrocarbon skeleton of the diisocyanate incorporated therein.

It is also an object of the present invention to provide processes for making such aromatic polyisocyanates.

These and other objects which will be apparent to those skilled in the art are accomplished with diisocyanates and mixtures of diisocyanates in which a major substituent is a diisocyanate corresponding to the general formula:

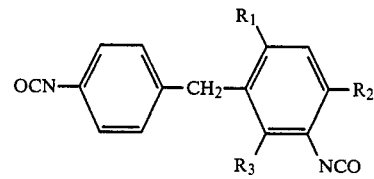

in which $R_1$, $R_2$ and $R_3$ may represent hydrogen or a $C_2$–$C_{12}$ alkyl group provided that at least two of the radicals $R_1$, $R_2$ and $R_3$ represent hydrogen and the third represents an alkyl group containing from 2 to 12 carbon atoms. These compounds are made by first reacting a nitrobenzyl halide with a nitroalkylbenzene or an alkylbenzene an unsubstituted benzyl halide or a benzyl alcohol in in the presence of a Friedel-Crafts catalyst with an alkylbenzene and then nitrating with the exception of those condensation products having already two nitro-groups, followed by hydrogenating or reducing the nitro groups to form the corresponding amino compound. The amino compound is then phosgenated to form the diisocyanate.

DETAILED DESCRIPTION OF THE INVENTION

The present invention relates to diisocyanates corresponding to the general formula:

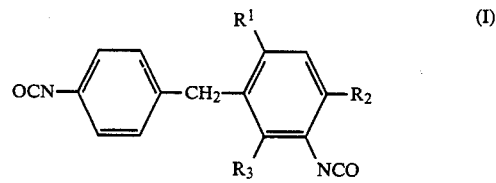

in which $R_1$, $R_2$ and $R_3$ may represent hydrogen or a $C_2$–$C_{12}$ alkyl group provided that two of the radicals $R_1$, $R_2$ and $R_3$ represent hydrogen and the third radical represents an alkyl group having from 2 to 12 carbon atoms, preferably 2 or 3 carbon atoms, most preferably an ethyl group.

The diisocyanate of the present invention may contain up to 40 wt% (based on total composition) diisocyanate corresponding to the general formula:

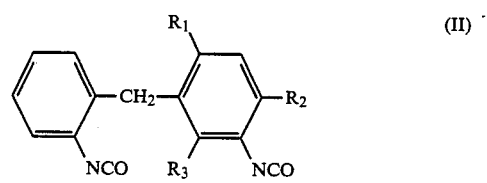

in which $R_1$, $R_2$ and $R_3$ are as defined above.

The diisocyanate of the present invention may also contain up to 40 wt% (based on total composition) other $C_2$–$C_{12}$ alkyl-substituted diisocyanato-diphenyl methane isomers.

The present invention also relates to the diisocyanate corresponding to the formula:

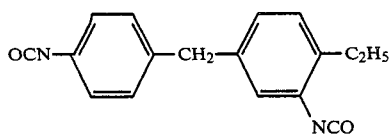

which diisocyanate is generally present as the main component in the ethyl-substituted diisocyanates or diisocyanate mixtures of the present invention. This compound may also be produced in pure form. The present invention also relates to the diisocyanate corresponding to the formula:

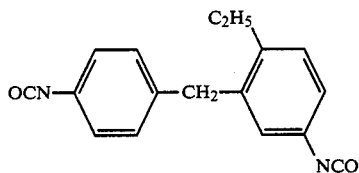

The present invention also relates to processes such as those described in detail below for producing these diisocyanates and diisocyanate mixtures which are useful as the isocyanate component in production of polyurethane plastics by the isocyanate polyaddition process.

The compounds according to the present invention, are diphenyl methane diisocyanates and mixtures containing substantial amounts of diphenyl methane diisocyanates having the structure indicated and containing a saturated alkyl substituent having from 2 to 12, preferably 2 or 3, most preferably 2, carbon atoms.

The composition of the diisocyanates and diisocyanate mixtures of the present invention, of the starting materials and of intermediate products may be determined by gas chromatography.

In one process for producing diisocyanates according to the present invention, a 4-nitrobenzyl halide is reacted in the presence of a Friedel-Crafts catalyst with 1-alkyl-2-nitrobenzene and/or 1-alkyl-4-nitrobenzene and/or technical mixtures of these nitrobenzene isomers (up to 15 wt. % based on the mixture as a whole may be 1-alkyl-3-nitrobenzene) to form a dinitro compound corresponding to the general formula:

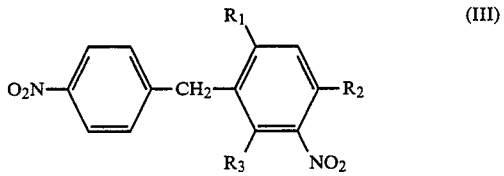

in which $R_1$, $R_2$ and $R_3$ are as defined above. Up to 20 wt. % of this reaction mixture may be made up of other isomeric dinitro-diphenyl methanes. After the dinitro has been formed, the Friedel-Crafts catalyst is removed from the reaction product. The dinitro compound thus obtained is then converted by hydrogenation or reduction of the nitro groups into the corresponding aromatic diamino compound. This diamino compound is then converted by phosgenation into the diisocyanate. The presence of any secondary products in the corresponding 3,4'-diamino- or 3,4'-diisocyanato-isomers may be substantially completely avoided by distillation of the diamines obtained before the phosgenation reaction and/or distillation of the diisocyanates after phosgenation.

As used herein, the terms "nitrobenzyl halide" and "benzyl halide" are to be understood to include all of the corresponding benzyl chlorides or bromides, particularly the corresponding benzyl chlorides.

Nitro- and alkyl-substituted benzenes suitable to the practice of the present invention include: the mononitration products of ethyl benzene, isopropyl benzene, n-propyl benzene, n-butyl benzene, n-octyl benzene and n-dodecyl benzene.

In the above-described process, a Friedel-Crafts condensation reaction takes place between the nitro-substituted alkyl benzene and 4-nitrobenzyl halide. The reactants are used in quantities such that from 1.0 to 20 moles (preferably from 2 to 10 moles) of nitro alkyl benzene are available for each mole of nitrobenzyl halide. The reactant used in excess also acts as solvent. The catalysts used are conventional Friedel-Crafts catalysts, such as aluminum chloride, iron trichloride, titanium tetrachloride and tin tetrachloride. Iron trichloride is the preferred catalyst. The Friedel-Crafts catalyst is generally used in a quantity which is from 1 to 100 mole percent (preferably from 5 to 50 mole percent) based on the benzyl halide component. The Friedel-Crafts condensation reaction is generally carried out at a temperature of from room temperature to the boiling point of the reaction mixture, i.e. from about 20° to about 200° C. (preferably from 30° to 120° C.). After the condensation reaction, the catalyst is removed (preferably by washing with a material such as water or dilute hydrochloric acid) and the excess, unreacted starting material is distilled off.

The nitro groups present in the product of the Friedel-Crafts condensation are then either hydrogenated or reduced to the corresponding aromatically bound amino groups. Reduction is preferably carried out by catalytic hydrogenation in the presence of a Raney nickel, platinum or palladium catalyst. Hydrogenation is generally carried out in alcoholic solution. Methanol, ethanol, isopropanal, toluene and mixtures thereof are appropriate solvents. The nitro compound to be hydrogenated is generally present in an amount such that it forms a 10 to 50%, by weight, solution. Hydrogenation is carried out at a temperature of from 20° to 150° C., preferably from 30° to 100° C. This reaction may be carried out under pressure. Conversion of the nitro groups into the corresponding amino groups may also be carried out by the known reduction process using a reducing agent such as iron, zinc or tin. After the nitro groups have been converted into the corresponding amino groups, the catalyst is removed (e.g. by filtration) and the solvent is distilled off.

The amine accumulating as residue after the solvent is distilled off may then be directly phosgenated. If particularly pure products are desired, however, the diamine or diamine mixture may be distilled to remove any secondary products from the amine or amine mixture before it is phosgenated. As used herein the term "secondary products" means the unidentified constituents boiling at temperatures lower and/or higher than the products or intermediate products of the present invention.

The phosgenation may be carried out by methods known to those in the art. Chlorobenzene or dichlorobenzene, for example, may be used as the solvent. After the auxiliary solvent has been distilled off, the products according to the present invention are left behind as residue. If desired, the diisocyanates thus produced may be subjected to distillation to remove any secondary products which may still be present.

If 1-alkyl-2-nitrobenzene is used as the starting material in the above-described process, it is possible to produce isomer mixtures which contain from about 20 to 50%, by weight, of 3,4'-diisocyanato-2-alkyl diphenyl methane and from about 50 to 80%, by weight, of 3,4'-diisocyanato-4-alkyl diphenyl methane. 1-alkyl-4-nitrobenzene may be used as the starting material to produce 3,4'-diisocyanato-6-alkyl diphenyl methane. The 3,4'-diisocyanato-4-aklyldiphenyl methanes may be obtained in pure form by crystallizing the 3,4'-dinitro-4-alkyl diphenyl methanes from the reaction product from the Friedel-Crafts condensation before converting the dinitro compound to the diamino compound. This purification by crystallization may be carried out by dissolving the nitro compound or mixture of nitro compounds based on 4-nitrobenzyl halide and o-nitro-alkyl benzene, (obtained after excess starting material has been distilled off) in boiling alcohol or ethyl acetate to form a saturated solution and leaving the solution to cool to room temperature. The desired isomer preferentially crystallizes out during cooling. The crystallization process may be repeated as often as required.

The diisocyanates and diisocyanate mixtures of the present invention may also be produced by a second process in which a 4-nitrobenzyl halide is reacted with an alkyl benzene in the presence of a Friedel-Crafts catalyst to form a mixture of mononitro compounds corresponding to the general formula:

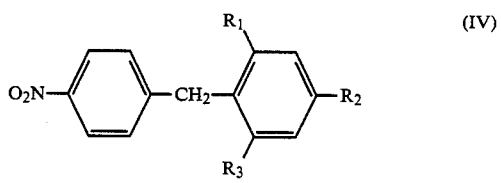

(IV)

in which $R_1$, $R_2$ and $R_3$ are as defined above. After this Friedel-Crafts condensation, the catalyst is removed from the reaction product. This mixture of mononitro compounds is then subjected to a nitration reaction to form dinitro compounds corresponding to the general formula:

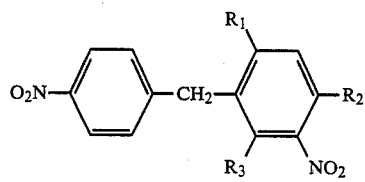

in which $R_1$, $R_2$ and $R_3$ are as defined above.

These dinitro compounds are then converted by hydrogenation or reduction of the amino groups into the corresponding aromatic diamino compounds. The diamino compounds thus obtained are converted by phosgenation into the corresponding diisocyanates. Any secondary products present in the 3,4'-diamino or 3,4'-diisocyanato-isomers may be removed from the diamines by distillation before the phosgenation reaction and/or from the diisocyanates by distillation after the phosgenation.

With the exception that alkyl benzene rather than an alkyl nitrobenzene is used as the starting material, the Friedel-Crafts condensation of this second process corresponds to that of the first process described above. It should be noted, however, that in general the boiling temperature of the alkyl benzene used in excess in the second process represents the upper limit of the temperature range. The catalyst-free condensation product obtained in this second process is then nitrated in accordance with techniques known to those in the art to form a mixture of isomeric dinitro compounds corresponding to general formula (III). Nitration may be carried out, for example, in the presence of a suitable solvent (such as methylene chloride) using "nitration acid", i.e. a mixture of concentrated sulphuric acid and nitric acid, preferably highly concentrated, approximately 98% nitric acid. The nitration acid is used in a quantity such that approximately 1.1 mole of nitric acid is available for each mole of mononitro compound. Nitration may generally be carried out at a temperature of from $-20°$ to $+80°$ C., preferably from $0°$ to $20°$ C. The organic phase present on completion of the nitration reaction may be removed from the acid by phase separation and washing with water and sodium carbonate solution, for example. The auxiliary solvent may then be removed by distillation, optionally followed by the removal of solvent residues using steam.

The thus-obtained dinitro compounds are further reacted in the same manner as the first process described above.

The diisocyanates made by this second process are generally mixtures containing from about 70 to 90 wt. % 3,4'-diisocyanato-2-, -4- or -6-alkyl diphenyl methane and from 10 to 40 wt. % of other analytically unidentified alkyl-substituted diisocyanato-diphenyl methane isomers. The product diisocyanates roughly correspond to the general formula:

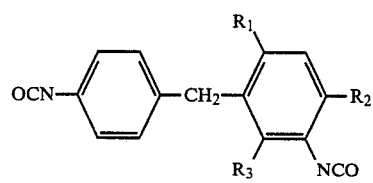

wherein one of the radicals $R_1$, $R_2$ or $R_3$ represents an alkyl group, and the other two represent hydrogen.

The diisocyanates or diisocyanate mixtures of the present invention may also be produced by a third process in which a benzyl halide or benzyl alcohol is reacted in the presence of a Friedel-Crafts catalyst or acid catalyst with an alkyl benzene to form a condensate made up of hydrocarbons corresponding to the general formula:

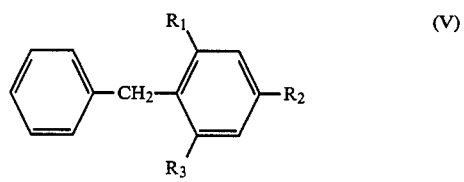

(V)

in which $R_1$, $R_2$ and $R_3$ are as defined above. The alkyl diphenyl methane isomer mixture corresponding to general formula (V) may then be removed from the condensate in pure form by distillation. This isomer mixture is then subjected to dinitration. The dinitro compounds thus obtained are subsequently converted by hydrogenation or reduction of the nitro groups into the corresponding diamines. These diamines are then converted by phosgenation into the corresponding diisocyanates. The corresponding 3,4'-isomer present in admixture with up to 40 wt %, of 2',3-isomers and with up to 40 wt % (based on the mixture as a whole) of other alkyl-substituted diisocyanato-diphenyl methane isomers may be recovered without substantial amounts of secondary products by distilling the diamines before phosgenation and/or distilling the diisocyanate mixture after phosgenation.

In this third process, an unsubstituted benzyl halide or benzyl alcohol is used as the reactant subjected to Friedel-Crafts condensation rather than the nitrobenzyl halide used in the first two processes described above.

When a benzyl halide is used, the Friedel-Crafts condensation reaction is carried out in the same manner as the first and second processes described above and within the same quantitative ratios between the reactants. However, it is preferred to use a molar ratio of alkyl benzene to benzyl chloride of from 5:1 to 20:1 with a molar ratio of from 8:1 to 15:1 being particularly preferred. In extreme cases, the Friedel-Crafts condensation reaction of this third process may be carried out in the gas phase at temperatures of up to 300° C. However, the preferred temperature for carrying out the condensation reaction is within the same range as that of the second process described above. When benzyl alcohol is used as the starting material, the catalysts which may be employed are substantially involatile strong acids, such as sulphuric acid and phosphoric acid. Fixed-bed catalysts containing sulfonic acid groups, such as ion exchangers containing sulfonic acid groups, or inorganic solid catalysts containing acid centers (Tonsils, Zeolites, etc.) may also be used.

The quantitative ratios between the reactants in this process are such that the alkyl benzene is used in excess to the same extent as the reactants subjected to Friedel-Craft condensation in the first and second processes described above. In this third process, the condensation reaction temperature is generally from −20° to +300° C., preferably from 20° to 110° C. The condensate which accumulates is separated from the catalyst (for example by washing out with water in the case of homogeneous catalysis or by filtration in the case of heterogeneous catalysis) and from the excess alkyl benzene (by distillation). This condensate may then be distilled to remove small quantities of compounds of higher molecular weight.

The thus-treated condensate is then subjected to dinitration in the same manner as in the second process described above. In this process, however, nitration acid is used in a quantity such that from 2.0 to 2.5 moles of nitric acid are present for each mole of hydrocarbon being nitrated.

The thus-obtained alkyl-substituted dinitro-diphenyl methane isomers are further processed in exactly the same way as in the first and second processes described above. The 4-alkyl-3,4'-isomer obtained in this third process may be purified by partial crystallization at the nitro stage, in the same manner as has been described above with respect to the first process of the present invention.

In the third process for making the diisocyanate of the present invention, diisocyanates corresponding to the general formula:

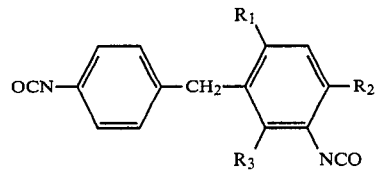

present in admixture with up to 40 wt % (preferably from 10 to 25 wt %) based on the mixture as a whole, of diisocyanates corresponding to the general formula:

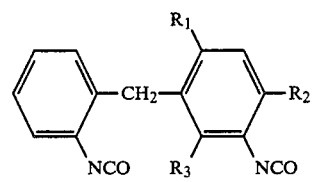

and with up to 40 wt % (based on the mixture as a whole) of other alkyl-substituted diisocyanato-diphenyl methane isomers are produced. In each of these general formulae one of the radicals $R_1$, $R_2$ or $R_3$ represents an alkyl group, and the other two radicals each represent hydrogen.

With the exception of the first process described above in which 1-alkyl-4-nitrobenzene is used as a starting material, mixtures of isomers differing from one another in the position of the alkyl substituent are always formed in the production of alkyl-substituted diisocyanates or diisocyanate mixtures. The 3,4'-diisocyanato-4-alkyl diphenyl methane of the present invention is, however, generally the main constituent. With respect to the properties of the diisocyanate mixtures of the present invention and their suitability for the production of polyurethanes, the position of the alkyl substituent and the particular percentage content of the respective isomers (distinguished by the position of the alkyl substituent) are of secondary importance. The polyisocyanate mixtures of the present invention are technical mixtures which often contain minor amounts (i.e. up to 40 wt. %) of constituents which cannot be clearly identified by analysis, specifically analysis by gas chromatography. The unidentified constituents are generally alkyl-substituted diisocyanato-diphenyl methane isomers having NCO-groups in the 2,4'-, 4,4'- or 3,3'-position, or mixtures of such isomers. These unidentified secondary products in the mixtures of the present invention do not in any way adversely affect the favorable properties of the diisocyanates if they are present in an amount within the quantitative limits specified above. All of the diisocyanates and diisocyanate mixtures of the present invention have the advantageous features of prior art materials such as TDI and MDI but do not require treatment (e.g. melting) before they can be used. Nor do they necessitate the strict safety precautions which must be taken when the prior art materials are used. The viscosity of the diisocyanates and diisocyanate mixtures of the present invention is generally from 10 to 50 mPa.s at 25° C.

The diisocyanates and diisocyanate mixtures of the present invention are particularly valuable starting materials for the production of polyurethane plastics. These diisocyanates and diisocyanate mixtures may be used as substitutes for TDI and/or MDI in known processes for the production of polyurethane plastics from TDI and/or MDI.

Having thus described our invention, the following examples are given by way of illustration. All percentages given in these examples represent percents by weight unless otherwise indicated.

EXAMPLE 1 (First process)

1(a) 171.5 g (1 mole) of 4-nitrobenzyl chloride were dissolved at room temperature in 755 g (5 moles) of 1-ethyl-2-nitrobenzene. 13.2 g (0.1 mole) of anhydrous aluminum trichloride were then added. The reaction mixture was slowly heated with stirring to 120° C. and maintained at that temperature until the evolution of hydrogen chloride had ceased. After a total of 8 hours, no more nitrobenzyl chloride was detected in the reaction mixture. After cooling to room temperature, the reaction mixture was diluted with 500 ml of methylene chloride, extracted once with 200 ml of dilute hydrochloric acid and washed 3 times with 500 ml of water. After drying, first the methylene chloride and then the excess 1-ethyl-2-nitrobenzene were separated off. The remaining material was then steam distilled.

According to analysis by gas chromatography, the residue (275 g) contained in its volatile fraction: 3.0%, unidentified binuclear dinitro compounds; 68.0% 4-ethyl-3,4'-dinitro-diphenyl methane; and 29.0% 2-methyl-3,4'-dinitro-diphenyl methane.

1(b) 250 g (0.875 mole) of the nitro product from 1(a) were dissolved in 600 ml of methanol. 30 g of fresh Raney nickel were then added to the resulting solution. This nitro compound containing solution was then reduced at 50° C. using hydrogen under 50 bars pressure until the pressure remained constant. On completion of the exothermic reaction, hydrogen pressure was maintained for 1 hour at 100° C./50 bars. The pressure was then relaxed, the catalyst was filtered off and methanol and water were distilled off. According to analysis by gas chromatography, the residue (199 g) contained 0.7% low-boiling products, 91.5% diamines, 7.8% higher boiling products 1(c) The crude amine (199 g) of 1(b) was dissolved in 125 ml of monochlorobenzene. The resulting solution was added dropwise to a solution of 400 g of phosgene in 1250 ml of monochlorobenzene with stirring and cooling to 0° C. The reaction mixture was then slowly heated while more phosgene was passed through while the reaction mixture was refluxed for 1 hour. The monochlorobenzene was then distilled off under a water jet vacuum and the isocyanate was distilled under further reduced pressure (0.1 Torr). After collection of a small amount of a first fraction (approximately 20 ml), a diisocyanate fraction (195 g, 0.7 mole) distilled over at from 158° to 163° C. A distillation residue of approximately 35 g was left. According to GC analysis, 97% of the diisocyanate fraction was a mixture of 2- and 4-ethyl-3,4'-diisocyanato-diphenyl methane (ratio, by weight, approximately 30:70) and a diisocyanate which was not fully identified (approximately 3%, by weight).

EXAMPLE 2 (First process)

2(a) 250 g (1.45 moles) of 4-nitrobenzyl chloride were mixed with 587 g (3.89 moles) of 1-ethyl-4-nitrobenzene until the mixture was homogeneous. 16.2 g (0.1 mole) of anhydrous iron (III) chloride were then added to the mixture. The reaction was carried out and the products treated in the same manner as in Example 1(a). The solid residue (357 g) which was purified by recrystallization from ethyl acetate/ethanol (1:1). Pure 6-ethyl-3,4'-dinitro-diphenyl methane (Mp. 125°–126° C.) was obtained.

(b) 40 g (0.14 mole) of the purified nitro compound of 2(a) converted into the amine (31 g=99% of the theoretical yield) by reduction using iron powder.

(c) The amine from 2(b) was converted to the corresponding isocyanate by phosgenation in the same manner as in Example 1(c). The isocyanate (37 g) was distilled under reduced pressure. The main fraction (33.5 g=0.12 mole) was 6-ethyl-3,4'-diisocyanato-diphenyl methane, a colorless liquid which has a boiling point of 158° C., an NCO-content of 30.2 wt %, and a hydrolyzable chlorine content of <0.01%.

EXAMPLE 3 (Second process)

3(a) 171.5 g (1 mole) of 4-nitrobenzyl chloride were dissolved in 263 g (2.5 moles) of dry ethyl benzene. The resulting solution was slowly added dropwise with stirring at 40° C. to 3 g of anhydrous iron (III) chloride in 800 g (7.5 moles) of dry ethyl benzene. The reaction mixture was then slowly heated to 80° C. and maintained at that temperature until the evolution of hydrogen chloride had stopped. The reaction mixture was then stirred for 2 hours at from 70° to 80° C. and cooled. After cooling, the mixture was washed 3 times with 500 ml of water until it was free of acid. After drying and removing the excess ethyl benzene by distillation, the residue (230 g) was distilled under reduced pressure (0.1 Torr). 227 g (94.2% of the theoretical yield) of low viscosity pale yellow oil distilled over at from 135° to 145° C., leaving 6 g of residue.

The above-described procedure was repeated using a 5:1 excess of ethyl benzene. 219 g (91% of the theoretical yield) of distilled product of substantially the same composition were recovered.

The GC-spectrum indicated that this product had the following composition: approximately 2%, unidentified compound, 55% 2-(and 3-)ethyl-4'-nitrodiphenyl methane and 45% 4-ethyl-4'-nitrodiphenyl methane.

3(b) 241.0 g (1 mole) of the distilled mixture of the 4-nitroethyl diphenyl methanes of 3(a) were introduced into 400 ml of methylene chloride at 20° C. Nitration acid consisting of a mixture of: 71 g (1.1 moles) of 98% $HNO_3$ and 110 g (1.1 moles) of 98% $H_2SO_4$ was added to this mixture with stirring and cooling to 20° C. On completion of the addition, the mixture was stirred for 60 minutes at 20° C., after which the nitration acid was separated off. The organic phase left behind was washed twice with 200 ml of water, once with 2% sodium carbonate solution and twice more with water. The methylene chloride was distilled off under normal pressure at a sump temperature of up to 90° C. and the solvent residues were removed using steam. The resulting product (274 g=96% of the theoretical yield) was freed from water in a water jet vacuum at 90° C./12 mm Hg. According to the GC analysis, the product contained in its volatile fraction: approximately 7.0% low-boiling constituents, 0.2% mononitrated ethyl diphenyl methanes and 92.6% dinitrated ethyl diphenyl methanes.

3(c) 250 g of the crude product from stage 3(b) were dissolved in 650 ml of methanol. 20 g of fresh Raney nickel were added to the resulting solution which was then reduced at 50° C. using hydrogen under 50 bars until the pressure remained constant. On completion of the exothermic reaction, hydrogen pressure was maintained for 1 hour at 80° C./50 bars. The pressure was then relaxed, the catalyst was filtered off and methanol and water distilled off up to 85° C./15 Torr. The residue of 190 g was distilled in a vacuum of 0.1 Torr. After a first fraction of 8 g (collected from 50° to 150° C.), 167 g of distillate were obtained as the main fraction at from 150° to 250° C., 11 g of residue remained.

According to analysis by gas chromatography, the main fraction contained: <1% low-boiling compound, 97-98% diamines and <2% higher nuclear compound.

(d) 165 g (0.75 mole) of the diamine fraction from 3(c) were converted into the corresponding isocyanates by phosgenation in the same manner as described above in Example 1(c).

The monochlorobenzene was then distilled off under a water jet vacuum and the isocyanate distilled under further reduced pressure (approximately 0.1 Torr). After a first fraction of approximately 25 ml, a diisocyanate fraction (189 g; 0.68 mole) distilled over at from 150° to 175° C. The distillation residue amounted to 12.5 g. According to gas chromatography, the diisocyanate fraction contained approximately 75% 2-, 4- and 6-ethyl-3,4'-diisocyanato-diphenyl methane and approximately 25% other isomers.

EXAMPLE 4 (Second process)

4(a) 171.5 g (1 mole) of 4-nitrobenzyl chloride were dissolved in 300 g (2.5 moles) of dry isopropyl benzene. The resulting solution was slowly added dropwise with stirring at 40° C. to 5 g of anhydrous iron (III) chloride in 900 g (7.5 moles) of dry isopropyl benzene. The reaction mixture was slowly heated to 90° C. and stirred until the evolution of HCl was almost over. Thereafter, the mixture was stirred for another hour at 90° C. The reaction product was worked-up in the same way as in Example 3(a). During distillation of the residue left after removal of the isopropyl benzene, 238 g (0.93 mole) of a fraction (of which 99%, by weight, was isopropyl-4-nitrodiphenyl methane, according to gas chromatography) distilled over at from 150° to 160° C./0.1 Torr. The distillation residue amounted to 6 g.

According to the gas chromatography analysis, the product composition was 54% 2-(and 3-)isopropyl-4'-nitrodiphenyl methane and 46% 4-isopropyl-4'-nitrodiphenyl methane.

This procedure was repeated using 5:1 isopropyl excess. 252 g (0.9 mole) of distilled product having substantially the same composition were produced.

4(b) 255 g (1 mole) of isopropyl-4-nitrodiphenyl methane from 4(a) were subjected to dinitration, followed by working-up in the same manner as described above in Example 3(b). According to gas chromatography, the crude product (282 g) contained in its volatile fraction: 9.2% low-boiling constituents, 11.0% mononitrated isopropyl diphenyl methanes, and 79.8% dinitrated isopropyl diphenyl methanes.

4(c) 250 g of the crude product from 4(b) were converted into the corresponding amine by reduction in the same manner as was described above in Example 3(c). 196 g of the amine were produced. The residue was then subjected to fractional distillation (Bp. 165°-195° C./0.1 Torr).

4(d) 140 g (0.5 mole) of the main fraction of the amines from 4(c) were converted into the isocyanate by phosgenation in the same manner as described above in Example 1(d).

The monochlorobenzene was then distilled off under a water jet vacuum and the isocyanate distilled under further reduced pressure (0.1 Torr). After a first fraction of approximately 15 ml (which contained chlorobenzene), a diisocyanate fraction of 131 g (0.48 mole) distilled over at from 160° to 165° C. The distillation residue amounted to 14 g.

According to the analysis by gas chromatography, the diisocyanate fraction had the following composition: approximately 65% isopropyl-3,4'-diisocyanatodiphenyl methanes, and approximately 35% other isomers. The isopropyl radicals of the main component were located in the 2-, 4- and 6-positions.

EXAMPLE 5 (Third process)

5(a) 10 g of anhydrous iron (III) chloride were added under nitrogen to 2.12 kg (20 moles) of dry ethyl benzene. 253 g (2 moles) of dry benzyl chloride were then added dropwise with stirring at 60° C. Gaseous hydrogen chloride evolved. On completion of this addition, the mixture was stirred for 60 minutes, cooled and washed 3 times with 500 ml of water until free from acid. The excess ethyl benzene was then separated off from the organic phase by distillation.

The residual hydrocarbon mixture (approximately 350 g) was determined by gas chromatography to contain: 82% binuclear isomers, 12-15% trinuclear isomers, and <5% higher nuclear constituents. First the binuclear fraction (153°-156° C./15 Torr) and then the trinuclear fraction (150°-175° C./0.1 Torr) were separated off by distillation under reduced pressure.

According to GC- and NMR-analysis, the binuclear fraction contained: approximately 40% 2-ethyl diphenyl methane and approximately 60% 4-ethyl diphenyl methane. 5(b) 294 g (1.5 moles) of the mixture of binuclear isomers of ethyl diphenyl methane obtained in 5(a) were introduced into 900 ml of methylene chloride at from 0° to 10° C. Nitration acid consisting of a mixture of: 209 g (3.25 moles) of 98% $HNO_3$ and 325 g (3.25 moles) of 98% $H_2SO_4$ was added with stirring anc cooling from 0° to 10° C. On completion of the addition, the mixture was stirred for 2 hours at 20° C. The nitration acid was then separated off. The organic phase was washed twice with 400 ml of water, once with 2% potassium carbonate solution and twice more with water. The methylene chloride was then distilled off under normal pressure at a sump temperature of up to 90° C. and the solvent residues were removed using steam. Water was removed under a water jet vacuum at a temperature of up to 100° C. The residue (401 g=93.5% of the theoretical yield, Mp. 40° C.) contained in its volatile fraction: 8.3% low-boiling constituents, <1% mononitrated ethyl diphenyl methanes and 91.3% dinitrated ethyl diphenyl methanes. The dinitro fraction contained from about 15 to 20% 2',3-dinitrocompounds; from 55 to 60% 3,4'-dinitro compounds and 30% other isomers.

5(c) 400 g of the crude mixture from the nitration of 5(b) were dissolved in 1000 ml of methanol. 40 g of fresh Raney nickel were added and the mixture subsequently reduced at 50° C. under a hydrogen pressure of 50 bars. On completion of the exothermic reaction, the hydrogen pressure was maintained at 100 bars for 1 hour at 100° C. The pressure was then released, the catalyst filtered off and methanol and water were distilled off. The residue was distilled under reduced pressure. A first fraction of approximately 50 g of low-boiling compounds containing residues of water was collected. Most of the amine mixture (258 g=1.14 mole) distilled over at from 160° to 200° C. (0.1 Torr). The residue in the distillation flask amounted to 15 g.

5(d) 250 g (1.1 mole) of the mixture of diaminoethyl diphenyl methanes (still contains <1% of monoamine) of 5(c) were dissolved in 1.25 liters of monochlorobenzene and the resulting solution slowly added dropwise with stirring and cooling (to 0° C.) to a solution of 400 g phosgene in 1.25 liters of monochlorobenzene. The reaction mixture was then slowly heated while more phosgene was passed through until the monochlorobenzene boiled under reflux. This mixture was kept boiling under reflux for 1 hour. After the monochlorobenzene had been distilled off under a water jet vacuum, the isocyanate was distilled under a reduced pressure of 0.1 Torr. After a first fraction of approximately 10 g had been collected the isomer mixture of the isocyanates (291 g, NCO-content 30.2 g) was obtained at from 155° to 175° C. in the form of a pale yellow oil which remained liquid even at 0° C. The distillation residue amounted to 10 g.

The isomer distribution of the diisocyanate fraction corresponds to the isomer distribution of the dinitro fraction of 5(b).

What is claimed is:

1. A process for the production of a diisocyanate corresponding to the general formula:

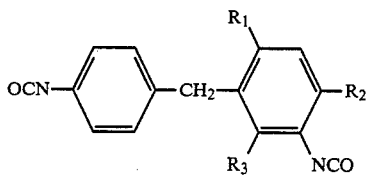

in which $R_1$, $R_2$ and $R_3$ represent hydrogen or a $C_2$–$C_{12}$ alkyl group provided that two of the radicals $R_1$, $R_2$ and $R_3$ represent hydrogen and the third represents an alkyl group having from 2–12 carbon atoms, comprising:
(a) reacting a 4-nitrobenzyl halide in the presence of a Friedel-Crafts catalyst with 1-alkyl-2-nitrobenzene and/or 1-alkyl-4-nitrobenzene and/or mixtures of these isomers and up to 15 wt % (based on whole mixture) 1-alkyl-3-nitrobenzene to form a dinitro compound corresponding to the general formula:

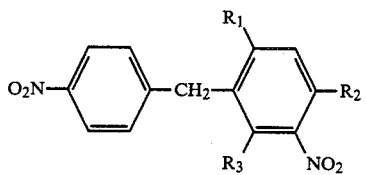

in which $R_1$, $R_2$ and $R_3$ are as defined above;
(b) separating the Friedel-Crafts catalyst from the product of (a);
(c) converting the product of (a) to a corresponding diamino compound by hydrogenating or reducing the nitro groups; and
(d) converting the diamino compound obtained in (c) to a diisocyanate by phosgenating the diamino compound.

2. The process of claim 1 wherein the reactants employed in (a) further comprise up to 20 wt. % of another isomeric dinitro-diphenyl methane.

3. The process of claim 1 wherein secondary products are removed from the diamino compound produced in (c) by distilling the diamino-compound containing mixture before phosgenation.

4. The process of claim 1 wherein secondary products are removed from the diisocyanate by distillation.

5. A process for the production of a diisocyanate corresponding to the general formula:

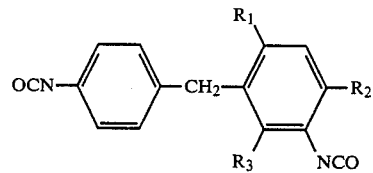

in which $R_1$, $R_2$ and $R_3$ represent hydrogen or a $C_2$–$C_{12}$ alkyl group provided that two of the radicals $R_1$, $R_2$ and $R_3$ represent hydrogen and the third represents an alkyl group having from 2–12 carbon atoms, comprising:
(a) reacting a 4-nitrobenzyl halide with an alkyl benzene in the presence of a Friedel-Crafts catalyst to form a mixture of mononitro compounds corresponding to the general formula:

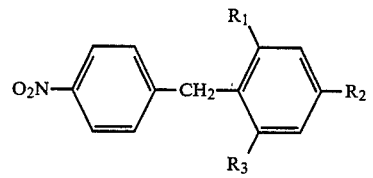

in which $R_1$, $R_2$ and $R_3$ are as defined above;
(b) separating the Friedel-Crafts catalyst from the product of (a);
(c) nitrating the product of (a) to form dinitro compounds corresponding to the general formula:

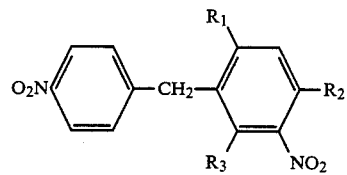

in which $R_1$, $R_2$ and $R_3$ are as defined above;
(d) converting the product of (c) to corresponding diamino compounds by hydrogenating or reducing the nitro groups; and
(e) converting the diamino compounds of (d) to corresponding diisocyanates by phosgenating the diamino compounds.

6. The process of claim 5 wherein secondary products are removed from the diamino compound of (d) by distillation before phosgenation.

7. The process of claim 5 wherein secondary products are removed from the diisocyanate by distillation.

8. A process for the production of a diisocyanate corresponding to the general formula:

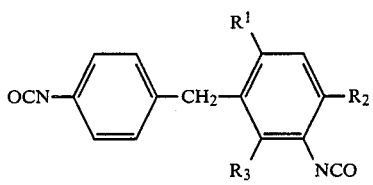

(I)

present in admixture with up to 40 wt % (based on mixture as a whole) of diisocyanate corresponding to the general formula:

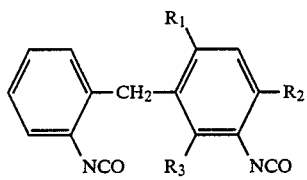

(II)

and up to 40 wt % (based on mixture as a whole) of other $C_2$-$C_{12}$ alkyl-substituted diisocyanato-diphenyl methane isomers
wherein $R_1$, $R_2$ and $R_3$ represent (in both formulae I and II), hydrogen or a $C_2$-$C_{12}$ alkyl-substituted group provided that two of the radicals $R_1$, $R_2$ and $R_3$ represent hydrogen and the third represents an alkyl group having from 2–12 carbon atoms comprising:
(a) reacting a benzyl halide or benzyl alcohol with an alkyl benzene in the presence of a catalyst to form a condensate containing substantial amounts of a compound corresponding to the general formula:

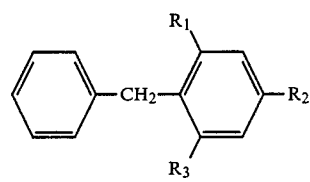

in which $R_1$, $R_2$ and $R_3$ are as defined above;
(b) distilling the condensate of (a) to obtain substantially pure alkyl diphenyl methane corresponding to the formula given in (a);
(c) nitrating the alkyl diphenyl methane of (b) to form a corresponding dinitro compound;
(d) converting the dinitro compound of (c) to a corresponding diamine by hydrogenating or reducing the nitro groups; and
(e) phosgenating the diamine of (d) to form a corresponding diisocyanate.

9. The process of claim 8 wherein the catalyst employed in (a) is a Friedel-Crafts catalyst.

10. The process of claim 8 wherein the catalyst employed in (a) is an acid catalyst.

11. The process of claim 8 wherein secondary products are removed from the diamino compound of (d) by distillation before phosgenation.

12. The process of claim 8 wherein secondary products are removed from the diisocyanate by distillation.

* * * * *